United States Patent [19]

Hasselbring

[11] Patent Number: 5,105,049
[45] Date of Patent: Apr. 14, 1992

[54] OLEFIN DIMERIZATION WITH HYDROGEN-TREATED CATALYSTS

[75] Inventor: Lori G. Hasselbring, Bartlesville, Okla.

[73] Assignee: Phillips Petroleum Company, Bartlesville, Okla.

[21] Appl. No.: 742,252

[22] Filed: Aug. 8, 1991

Related U.S. Application Data

[62] Division of Ser. No. 608,853, Nov. 5, 1990, Pat. No. 5,081,093.

[51] Int. Cl.$^5$ .............................................. C07C 2/24
[52] U.S. Cl. ................................................... 585/516
[58] Field of Search ............... 585/516, 511, 508, 520, 585/530; 502/174, 330

[56] References Cited

U.S. PATENT DOCUMENTS

| | | | |
|---|---|---|---|
| 2,881,234 | 4/1959 | Esmay et al. | 260/683.15 |
| 2,952,719 | 9/1960 | Appell | 260/683.2 |
| 2,986,588 | 5/1961 | Schramm | 260/683.5 |
| 3,104,271 | 9/1963 | Lindsay | 260/683.15 |
| 3,207,812 | 9/1965 | Hambling et al. | 260/683.15 |
| 3,260,770 | 7/1966 | Hambling et al. | 260/683.15 |
| 3,424,816 | 1/1969 | Hambling et al. | 260/683.15 |
| 3,594,441 | 7/1971 | Grebell et al. | 585/511 |
| 4,388,480 | 6/1983 | Imai et al. | 585/516 |
| 4,810,688 | 3/1989 | Ewart et al. | 502/174 |

FOREIGN PATENT DOCUMENTS 978590 12/1964 United Kingdom.
1167858 10/1969 United Kingdom ................ 585/511

OTHER PUBLICATIONS

Shaw et al., Carbanion Chemistry, I. Propylene Dimerization to 4-Methyl-1-pentent, J. Org. Chem. vol. 30, p. 3286 (1965).
Wilkes, Dimerization of Propylene to 4-Methyl-1-Pentene with Catalysts Derived from Potassium, Proceedings of the 7th World Petroleum Congress, vol. 5, pp. 299-308 (1967).

Primary Examiner—W. J. Shine
Assistant Examiner—Douglas J. McGinty
Attorney, Agent, or Firm—Lynda S. Jolly

[57] ABSTRACT

Olefin dimerization process comprises catalyst systems and supports. Catalyst supports are prepared from extruding alkali metal carbonate and a liquid. Optionally, the extruded catalyst support further comprises a carbonaceous compound. Catalyst systems comprise at least one elemental alkali metal deposited on the extruded catalyst support. Optionally, the catalyst system further comprises of at least one promotor. A hydrided catalyst system is prepared by contacting the catalyst system with hydrogen to reduce the dimerization induction period.

18 Claims, No Drawings

OLEFIN DIMERIZATION WITH HYDROGEN-TREATED CATALYSTS

BACKGROUND OF THE INVENTION

This case is a divisional application of U.S. Ser. No. 07/608,853, filed Nov. 5, 1990, now U.S. Pat. No. 5,081,903.

This invention relates to alkali metal carbonate supported alkali metal catalysts.

It is known in the art to employ alkali metal carbonate supported elemental alkali metal catalyst systems for such conversions as propylene dimerization. Several catalyst compositions, as well as methods of preparing these types of catalysts, are known in the art. The resultant catalyst systems, although useful to dimerize olefins, often have long induction periods before attaining maximum conversion to the desired product(s), representing a loss in product production. Thus, a dimerization process, because of longer induction times, can be more time consuming and more uneconomical.

SUMMARY OF THE INVENTION

It is an object of this invention to provide an improved catalyst system for the dimerization of the olefins.

It is another object of this invention to provide a method to prepare an improved alkali metal carbonate supported elemental alkali metal catalyst system, by the addition of hydrogen.

It is yet another object of this invention to provide a process to reduce the induction period for the dimerization of olefins.

It is yet another object of this invention to provide an improved process for the dimerization of olefins.

In accordance with this invention, a hydrided catalyst system comprising an extruded alkali metal carbonate support contacted with at least one elemental alkali metal, wherein said catalyst system is subsequently contacted with hydrogen, is provided. This hydrided catalyst system is useful to dimerize olefins and results in a reduced induction period.

In accordance with another embodiment of this invention, the dimerization catalyst system can further comprise at least one promoter.

DESCRIPTION OF THE PREFERRED EMBODIMENTS

The present invention provides a process to prepare an extruded catalyst support which comprises the steps of preparing a thick paste comprising alkali metal carbonate, a liquid, and optionally a carbonaceous compound, finely divided stainless steel, and/or a non-acidic inorganic oxide; forming an extrudate frog said paste; and calcining said extrudate to form an extruded catalyst support. After calcination, the extruded catalyst support is contacted with at least one elemental alkali metal, and optionally a promoter, to produce a catalyst system. The final hydrided catalyst system is prepared by a subsequent contacting with hydrogen. The hydrided catalyst system can be used to catalyze dimerization reactions.

SUPPORTS

The present invention provides a hydrided catalyst system using an extrude catalyst support contacted with an alkali metal and finally contacted with hydrogen to reduce the induction period of the dimerization reaction. A major advantage of using an extruded catalyst support rather than granules or pellets is longer catalyst life, since the extrudate retains its physical integrity under reaction conditions for longer periods of time than other types of catalyst supports. Granules and pellets can break up into fines after less than one day. In addition, elemental alkali metal forms a more uniform coating on the surface of an extruded support. The greater porosity of the extrudate allows an elemental alkali metal to permeate the center of the support as well as the surface. While not wishing to be bound by a theory, it is thought that an intermediate alkali metal hydride is formed which then produces an active species, alkali metal allyl. Dimerization reactions seem to initiate more quickly than those proceeding from the alkali metal directly to the alkali metal allyl.

The alkali metal carbonate portion of the extruded catalyst support of the invention can be any commercially available alkali metal carbonate with a particle size small enough to form a thick paste. Exemplary alkali metal carbonates include carbonates of lithium, sodium potassium, rubidium, cesium, and mixtures thereof. Potassium carbonate is the most preferred alkali metal carbonate due to ease of use and good compatibility with the preferred elemental alkali metal.

One particular technique for preparation of the extruded catalyst support is to form a thick paste comprising alkali metal carbonate and a liquid. In most cases the liquid can be water; or mixtures of water and alcohols; or water and water soluble ketones. It too much or too little liquid is used, it can be difficult to form an extruded product from the thick paste. Therefore, a solids to liquid ratio, based on weight, is generally at least about 3.5 parts solids mixed with about 1 part water, preferably about 3 parts solids mixed with 1 part water. The most preferred solids to liquid ratio is within the range of 1 t o2.5 parts solids mixed with 1 part liquid. However this weight ratio can vary depending on the particular components of the thick paste and ease of processing the thick paste for a particular product.

The thick paste is then extruded. The extrudate can be any diameter, but for best catalytic activity and ease of handling and processability, the extrudate is from about 1/16 to about ¼ inches in diameter. After the extrudate passes through the die, the extrudate can be cut into uniform lengths if desired. However, uniform lengths are not always necessary, to the extrudate can be allowed to break on its own, into any length, if the extrudate is allowed to break on its own, it will usually have a length of about 2 to about 7 times the diameter width. Usually, the extrudate is allowed to break of its own accord because of ease of manufacture.

The resultant material can then be dried under conditions of time and temperature sufficient to remove substantially all liquid. Usually, an oven is used, within a temperature range of about 80° to about 350° C., preferably a temperature within the range of about 85° to about 150° C., for at least 2 hours is sufficient. Drying can occur under any atmosphere, but for safety reasons, a vacuum oven is usually employed.

An extrusion process using alcohol and water as liquid is disclosed in Ewert et al, U.S. Pat. No. 4,810,688, herein incorporated by reference. Alcohols suitable for use in preparation of extruded catalyst supports are straight chain and branched aliphatic alcohols having from about 1 to about 7 carbon atoms. An extrusion process using water soluble ketones and water is disclosed in Drake, U.S. Pat. No. 4,895,819, herein incorporated by reference. Water soluble ketones suitable for use in preparation of extruded catalyst supports are straight chain and branched water soluble ketones having from about 3 to about 7 carbon atoms.

In accordance with another technique for the extruder catalyst support preparation, an alkali metal carbonate, a liquid and at least one carbonaceous compound are mixed and then extruded. The term "carbonaceous compound" is intended to include various forms of elemental carbon. Examples include, but are not limited to, carbon black, charcoal, coconut charcoal, amorphous graphite, and crystallite graphite. The extruded catalyst support is then heated in an oxygen-containing atmosphere under conditions suitable to oxidize in the range of about 10 to about 90 weight percent of the carbonaceous compound. As a result of the partial oxidation of the extruded catalyst support, the concentration of carbonaceous compound remaining on the surface of the support is substantially less than the concentration of carbonaceous compound remaining on the interior portions of the support. Catalyst supports prepared in his manner will be referred to as "extruded carbon containing" alkali metal carbonate supports.

Once the catalyst support is extruded and dried, the extruded catalyst support must be calcined in an oxygen-containing atmosphere at a temperature within the range of about 100° to about 500° C., preferably from about 150° to about 400° C., and most preferably from about 175° to about 350° C. for a time of at least 2 hours. The temperature needs to be high enough to drive off any remaining liquid from the surface and pores of the support. If the temperature is too high, the support can melt and eliminate all porosity resulting in low activity catalyst. Times in excess of about 20 hours generally impart no additional beneficial affect. Thus, times in the range of about 2 to about 20 hours are useful. Upon completion of calcination, the extruded catalyst support can be stored in a dry atmosphere. Preferably, the extruded catalyst support is stored under a dry, oxygen-free atmosphere until needed for further treatment.

CATALYST SYSTEMS

Catalyst systems employed in the practice of this invention comprise one of the extruded catalyst supports described above, at least one elemental alkali metal catalyst, and optionally one or more additional promoters. It should be recognized, however, that the catalyst systems of the invention can contain additional components which do not adversely affect the catalyst performance, such as, for example, pigments, dyes, processing aids, inert fillers, binders and the like.

The elemental alkali metals, also referred to as "alkali metals", contemplated to be within the scope of the invention include lithium, sodium, potassium, rubidium, and cesium. While the proportion of alkali metal combined with the extruded catalyst support can vary appreciably, generally at least about one weight percent of alkali metal based on the total weight of the extruded catalyst support will be employed. Generally, about 1 to about 20 weight percent alkali metal will be employed with about 2 to about 15 weight percent preferred. An alkali metal loading of about 3 to about 10 weight percent based on the total weight of the extruded catalyst support is most preferred for most efficient use of reagents, high catalyst activity and selectivity, high isomer ratio, and ease of catalyst preparation. Potassium is the preferred elemental alkali metal due to its ready availability as well as excellent compatibility with the inventive catalyst support.

The promoters contemplated to be within the scope of the invention include elemental copper, elemental cobalt, finely divided stainless steel, finely divided glass, and mixtures of two or more thereof. The proportion of optional promoter on the alkali metal carbonate support can vary appreciably, but generally, at least one weight percent of the optional promoter based on the total weight of extruded catalyst support will be employed. The following amounts are provided for additional guidance:

| Promoter | Loading, Weight Percent | | |
| --- | --- | --- | --- |
| | Broad | Intermediate | Preferred |
| Cu | 1-30 | 3-20 | 5-12 |
| Co | 1-50 | 3-25 | 5-15 |
| *SS | 1-80 | 3-60 | 5-50 |
| Glass | 1-50 | 2-25 | 3-15 |

*SS = Stainless Steel

The general procedure for preparation of the catalyst systems of the invention, after calcining the support, involves heating the extruded catalyst support to a temperature in the range of about 80° to about 350° C., preferably slightly above the melting point of the particular alkali metal used and then contacting the support with at least one elemental alkali metal in a dry, oxygen-free atmosphere, such as, for example $N_2$, Ar, or the like. The contacting, done in an oxygen-free atmosphere, is preferably carried out with suitable mixing to ensure even distribution. Suitable temperatures for the contacting step will vary with the particular alkali metal employed. For example, with elemental potassium, temperature in the range of about 80° to 120° C. are preferred, while with elemental sodium, temperatures in the range of about 100° to 140° C. are preferred.

While the catalyst system is maintained at or above the melting point of the particular alkali metal used, in an oxygen-free atmosphere, any desired promoter(s) can be gradually added while the treated catalyst is continually stirred. For example, with potassium, temperatures in the range of about 80° to about 120° C. are employed. The catalyst system is then ready to be contacted with hydrogen.

Optionally, the catalyst system, once elemental alkali metal and any desired promoters have been contacted, can be subjected to a subsequent heating step, in an oxygen-free atmosphere, to ensure as uniform a distribution as possible of the various promoters on the surface of the alkali metal carbonate support. Thus, the finished catalyst system can be subjected to a temperature in the range of about 80° to about 350° C. for a time in the range of about 0.1 to about 4 hours. A temperature in the range of about 150° to about 250° C. for a time in the range of about 0.5 to about 2 hours is presently preferred for the most uniform distribution.

Optionally, prior to charging the reactor, the catalyst system can be mixed with an inert substance to dilute the catalyst system and decrease the rate of olefin dimerization. Any inert substance which has no catalytic activity in an olefin dimerization reaction can be used. One example of such an inert substance is glass beads.

As indicated by the variety of supports, alkali metal components, and promoters included within the scope of the invention, numerous catalyst system combinations are possible. Any combination of the alkali metal and optional promoters disclosed can be supported on any alkali metal carbonate support disclosed. Some possible combinations are described in detail in the examples which follow. The combination of extruded support, alkali metal and promoter(s) which one may choose to employ will depend on a variety of variables such as for example, reactor configuration, reaction temperature and pressure, olefin feed employed, rate of olefin feed, and conversions desired.

HYDROGEN TREATMENT

Once the catalyst system is prepared, it is then contacted with hydrogen in either a continuous or a batch fashion. As used in this disclosure, the term "hydrogen" includes any hydrogen-donating species. Exemplary compounds include, but are not limited to, hydrogen ($H_2$), lithium aluminum hydride ($LiAlH_4$), and/or calcium hydride ($CaH_2$). Preferably, due to ease of use and availability, hydrogen ($H_2$) is used. Hydrogen ($H_2$) is also preferred because $H_2$ is highly reactive and does not have a detrimental affect on the dimerization catalyst system.

The contacting temperature can vary depending on the catalyst and feed(s) employed. Typically, a temperature range of about 50° to about 250° C. is suitable. Temperatures of about 80° to about 200° C. are preferred, with a range of about 120° to about 170° C. most preferred because optimum contacting conditions are obtained with minimum disruption of the catalyst system. Therefore, a more effective catalyst system is produced.

Pressure during the hydrogen contacting can vary widely. Pressures of atmospheric up to about 10,000 psig and higher are suitable. Preferably, pressures of about 100 to about 5,000 psig are employed, with pressures of about 100 to about 4,000 psig most preferred in order to achieve a good balance between reducing the reaction induction time and minimizing equipment and operating costs necessitated by very high contacting pressures.

The contact time required for hydrogen contacting depends upon several factors, such as, for example, the activity of the non-hydrided catalyst system, temperature, and pressure. The length of time during which hydrogen is contacted with catalyst can vary conveniently between about 0.1 seconds and about 24 hours although shorter and longer contact times can be employed. Preferably, times of about one minute to about 12 hours are employed. The most preferred contacting time is about 30 minutes to about eight hours to allow sufficient time to produce the desired effect of reducing the induction period without providing unnecessary and uneconomical exposure time.

Where contacting is carried out in continuous fashion, it is convenient to express the hydrogen/catalyst contact time in terms of weight hourly space velocity (WHSV), i.e., the ratio of the weight of hydrogen which comes in contact with a given weight of catalyst per unit time. Thus, a WHSV of about 0.1 to about 10 will be employed. A WHSV of about 0.5 to about 5 is preferred, with abut 1 to about 4 WHSV most preferred for optimum catalyst productivity.

Once hydriding, or contacting, is complete, the reactor is purged with an inert gas, such as nitrogen or argon, before introducing the reactants.

REACTANTS

Reactants applicable for use in the process of the invention are olefinic compounds which can (a) self-react, i.e., dimerize, to give useful products such as, for example, the self-reaction of propylene gives 4-methyl-1-pentene; and/or (b) olefinic compounds which can react with other olefinic compounds, i.e., co-dimerize, to give useful products such as, for example, co-dimerization of ethylene plus propylene gives 1-pentene, co-dimerization of ethylene and 1-butene gives 3-methyl-1-pentene and so forth. As used herein, the term "dimerization" is intended t include both self-reaction and "co-dimerization" as defined above.

Suitable dimerizable olefinic compounds are those compounds having from about 3 to about 30 carbon atoms and having at least one olefinic double bond and at least one allylic hydrogen atom, i.e., at least one hydrogen atom attached to a carbon atom adjacent to a double-bonded carbon atom. Exemplary compounds include, but are not limited to, acyclic and cyclic olefins such as, for example, propylene, 1-butene, 2-butene, isobutylene, 1-pentene, 2-pentene, 1-hexene, 2-hexene, 3-hexene, 1-heptene, 2-heptene, 3-heptene, the four normal octenes, the four normal nonenes and so forth; 3-methyl-1-butene, 2-methyl-2-butene, 3-methyl-1-pentene, 3-methyl-2-pentene, 4-methyl-1-pentene, 4-methyl-2-pentene, tetramethylethylene and the like; cyclopentene, cyclohexene, methylcyclopentene, methylcyclohexene, and the like and mixtures of any two or more thereof.

Suitable co-dimerizable olefinic compounds are those compounds having from about 2 to about 30 carbon atoms, including all the compounds contemplated within the scope of "dimerizable" olefinic compounds as indicated above. In addition, olefinic compounds which do not have at least one allylic hydrogen atom are also included within the scope of co-dimerizable olefins. Exemplary compounds in addition to those indicated above, include, but are not limited to ethylene, 3,3-dimethyl-1-butene, ditertiarybutyl ethylene and the like and mixtures of any two or more thereof.

The compounds indicated above as dimerizable olefinic compounds are capable of undergoing both self-reaction, i.e., dimerization, and cross-reaction, i.e., co-dimerization, with other members of the same group or with those compounds designated as co-dimerizable. The co-dimerizable compounds which do not have at least one allylic hydrogen may be capable of isomerization to form an olefin having an allylic hydrogen under the reaction conditions employed. If such isomerization is not possible, then those non-isomerizable, co-dimerizable compounds which do not have at least one allylic hydrogen must be contacted with at least one of the "dimerizable" compounds in order to facilitate the desired co-dimerization reaction. In other words, the co-dimerizable compounds which do not have at least one allylic hydrogen atom and are not capable of isomerization to produce an olefin having at least one allylic hydrogen are therefore not capable of reacting with themselves under the reaction conditions employed for the dimerization reaction.

REACTION CONDITIONS

The dimerization reaction of the invention can be carried out using either batch or continuous types of operation, although the catalysts of the invention are particularly well suited for continuous, fixed bed, operation. Suitable equipment, such as, for example, autoclaves, tubular reactors and the like as are well known in the art can be employed. No special materials of construction are required so that steel, stainless steel, glass-lined reactors, or the like can be employed.

The reaction temperature can vary depending on the catalyst and feed(s) employed. Typically, a temperature range of about 50° to about 250° C. is suitable. Temperatures of about 80° to about 200° C. are preferred with a range of about 120° to about 170° C. most preferred because optimum reaction rates are obtained with minimum by-product formation.

The dimerization reaction can be carried out by contacting the dimerizable olefins with catalyst in the liquid phase or the gas phase, depending on the structure and molecular weight of the olefin, as well as reaction temperature and pressure employed. Pressure during the dimerization reaction can vary between wide limits. In general, higher pressures favor the progress of the reaction. Thus, pressures of atmospheric up to about 10,000 psig and higher are suitable. Preferably, pressures of about 100 to about 5,000 psig are employed, with pressures of about 1,000 to about 4,000 psig most preferred in order to achieve a good balance between reaction rate and minimize equipment and operating costs necessitated by very high reaction pressures.

If the reaction is carried out in the liquid phase, solvents or diluents for the reactants can be used. Saturated aliphatic hydrocarbons, e.g., pentane, hexane, cyclohexane, dodecane; aromatic compounds, preferably those without an alpha-hydrogen (which would be capable of undergoing alkylation under the reaction conditions) such as benzene and chlorobenzene are suitable. If the reaction is carried out in the gaseous phase, diluents such as aliphatic hydrocarbons, for example methane, ethane and/or substantially inert gases, e.g., nitrogen, argon, can be present.

The contact time required for the dimerization reaction depends upon several factors, such as, for example, the activity of the catalyst, temperature, pressure, structure of the reactants employed, level of conversion desired, and the like. The length of time during which the dimerizable olefinic compounds are contacted with catalyst can vary conveniently between about 0.1 seconds and about 24 hours although shorter and longer contact times can be employed. Preferably, times of about one minute to about 5 hours are employed. Where reaction is carried out in continuous fashion, it is convenient to express the reactant/catalyst contact time in terms of weight hourly spaced velocity (WHSV), i.e., the ratio of the weight of reactant which comes in contact with a given weight of catalyst per unit time. Thus, a WHSV of about 0.1 to about 10 will be employed. A WHSV of about 0.5 to about 5 is preferred, with about 1 to about 4 WHSV most preferred for optimum catalyst productivity.

PRODUCTS

The olefinic products of the invention have established utility in a wide variety of applications, such as, for example, as monomers for use in the preparation of homopolymers, copolymers, terpolymers, e.g., as the third component of ethylene-propylene terpolymers useful as synthetic elastomers, and the like.

A further understanding of the present invention and its advantages will be provided by reference to the following examples.

EXAMPLES

An extruded catalyst support was prepared from commercially available anhydrous potassium carbonate (JT Baker, ACS reagent grade) and deionized water. The solid components had a particle size of equal to or less than about 0.42 mm (40 mesh). Sufficient water was added to the solid particles to form a thick paste. Usually, about 1 milliliter of water was added to about 3.5 grams of solid material. The thick paste was thoroughly mixed and formed into an extrudate and then dried at about 85° C. in a vacuum oven for at least two hours in the presence of air. The extrudate was calcined at about 175° to abut 375° C. for about 2 to about 5 hours in an oxygen-containing atmosphere.

The resultant extruded catalyst support was allowed to cool and maintained at a temperature of about 100° C. in an oxygen-free atmosphere, at which time about 4 to about 8 weight percent of elemental potassium based on the weight of the calcined support was added while mixing. In addition, an amount of inert material, equal to the amount of calcined support, was mixed with the 8% catalyst system to adjust the total percent potassium to about 4–5%, as further discussed below. The catalyst support and catalyst systems were kept under a dry, inert atmosphere at all times during and after preparation.

In Examples I, II, and IV, the hydrogen contacting of the catalyst system and subsequent dimerization of propylene were carried out in a steam heated 316 stainless steel tubular reactor ($\frac{1}{2}"\times 20"$). The catalyst system (density about 0.84 g/mL), was bounded above and below by small volumes of glass beads. The 8% potassium catalyst systems, in Example I and Runs 201 and 202 of Example II, were combined with 25 grams of an inert substance, i.e., no dimerization catalytic activity, to keep the amount of potassium in he reactor consistent at 4–5%. The 4–5% catalyst systems of Runs 203–206 and Examples III and IV did not contain inert substances.

The contents of the tubular reactor were heated to the contacting temperature of about 160° C. and contacted with hydrogen at varying times and pressures. The system was purged with nitrogen and conditions were adjusted to a pressure of about 1500 psig and a temperature of about 160° C. prior to the introduction of propylene. Propylene was then pumped into the reactor at a rate of about 120 mL/hr. After about 1.5 hours of reaction time and each one hour thereafter, until maximum conversion was achieved, a sample was collected and analyzed by gas liquid chromatograph (GLC). The summarized results represent the maximum analysis of the sample collected.

Catalyst systems and the results of the corresponding propylene dimerizations are summarized in Table I. Induction period is the amount of time required from the start of the reaction to the time when maximum conversion is attained. Percent propylene conversion is the weight percent of reactant propylene that was converted to any type of reaction product consisting of six carbon atoms. Percent selectivity is the weight percent of said product that was converted to 4-methyl-1-pentene (4-MP1). The isomer ratio, 4-methyl-1-pentene/4-methyl-2-pentene (4-MP1/4MP2), is the mass ratio of 4MP1 to 4MP2 in the final product. The isomer ratio data is significant because 4MP1, the desired product, and 4MP2, the undesired product, are difficult to separate.

EXAMPLE I

TABLE I

| | Hydrogen Treatment of Extruded Catalyst Systems* | | | |
|---|---|---|---|---|
| Run No. | $H_2$ Treatment at 160° C. | Induction Period (Hrs) | Maximum Conversion, % | Selectivity, % | 4MP1/4MP2 |
| 101 | NONE | 18.8 | 36 | 89 | 24 |
| 102 | 600 psig/3 hrs | 9 | 32 | 89 | 23 |
| 103 | 1000 psig/1 hrs | 7.5 | 33 | 89 | 21 |
| 104 | 1000 psig/3 hrs | 4.5 | 32 | 88 | 20 |
| 105 | 1500 psig/0.5 hrs | 11 | 33 | 89 | 22 |
| 106 | 1500 psig/1 hrs | 4.5 | 36 | 88 | 19 |
| 107 | 1500 psig/3 hrs | 4.5 | 36 | 88 | 18 |
| 108 | 1500 psig/6 hrs | 5.5 | 33 | 88 | 20 |

*8% K by weight, based on weight of extruded catalyst support

The data in Table I show that the best overall hydrogen contacting conditions are those in Runs 104, 106 and 107 based on the reduced induction period, while still maintaining reasonably high levels of percent conversion, selectivity and isomer ratio, although other treatments are effective at reducing the induction period. Run 101, where hydrogen treatment is absent, demonstrates an induction period which is four times longer than Run 104, 106, and 107 where hydrogen treatment is at a pressure of from 1000 to 1500 psig for a period of time ranging from about one to about three hours.

EXAMPLE II

TABLE II

| | Hydrogen Treatment of Various Support Forms at 160° C.,/1500 psig/3 hrs | | | |
|---|---|---|---|---|
| Run | Catalyst* | Induction Time (hrs) | Maximum Conversion, % | Selectivity % | 4MP1/4MP2 Ratio |
| 201 | 8% K no $H_2$ Extrudate | 18.8 | 36 | 89 | 24 |
| 202 | 8% K with $H_2$ Extrudate | 4.5 | 36 | 88 | 18 |
| 203 | 4% K no $H_2$ Granules | 19 | 54 | 86 | 11 |
| 204 | 4% K with $H_2$ Granules | 16 | 55 | 88 | 13 |
| 205 | 5% K no $H_2$ Pellets | 22.5 | 46 | 88 | 17 |
| 206 | 5% K with $H_2$ Pellets | 21.5 | 51 | 88 | 17 |

*% by weight, based on weight of extruded catalyst support

The data in Table II show the reduction in induction period on the extruded catalyst system, comparing runs 201 and 202. Runs 204 and 206, using granules and pellets do not show a similar decrease over Runs 203 and 205 respectively.

EXAMPLE III

Example III was conducted in two cooled-tube reactors, 15 feet in height and 3 inches in diameter, constructed of 316 stainless steel. Cooled tube reactors 1 and 2 were loaded with 22-23 lbs of 4% potassium catalyst system, based on the weight of the extruded potassium carbonate support. No inert substance was included. The catalyst in reactor 1 was treated with static hydrogen at 150° C. and 1445 psig for three hours. Reactor 1 was then purged with nitrogen and cooled to room temperature. Reactor 2 was not treated with hydrogen. Both reactors were brought up to a temperature of 160° C. under flowing propane, before switching to propylene. The propylene feed stream to the reactors was preheated to nominally 150° C. at 1400 psig at 3 WHSV propylene feed. The reactor was maintained at isothermal conditions using a heat transfer media to absorb the heat of reaction. The reactor effluent was cooled to 120° F. (49° C.) and sampled approximately every two hours until maximum conversion was obtained and analyzed by gas liquid chromatography.

This particular untreated catalyst did not show the usual long induction times. Previous induction times of 2-6 days were typical in the larger scale reactors. However, both the hydrogen treated and untreated catalyst systems of Example III exhibited an induction period of only 5 hours. The shorter induction period may be due to the use of different support extrusion apparatus in preparing catalyst systems for the larger scale reactors.

TABLE III

| Larger Scale Reactor Results of Hydrogen Treatment | | | | |
|---|---|---|---|---|
| Catalyst (WHSV = $hr^{-1}$) | Induction Period (hours) | Maximum Propylene Conversion (%) | 4MP1 Selectivity (%) | 4MP1/4MP2 |
| Standard (3.0) | 5.5 | 9 | 91 | 60 |
| $H_2$-treated (3.0) | 5.5 | 10 | 91 | 52 |

EXAMPLE IV

Example IV reaction conditions are the same as those described for Examples I and II. However, the catalyst system used was the same 4% K by weight based on the extruded catalyst support used in the larger scale reactors described in Example III.

TABLE IV

| Laboratory Data on Catalyst used in Larger Scale Reactors | | | | |
|---|---|---|---|---|
| Catalyst[a] (WHSV = $hr^{-1}$) | Induction Period, hours | Maximum Propylene Conversion, % | 4MP1 Selectivity, % | 4MP1/4MP2 |
| Standard (1.4) | 5.0[b] | 11 | 88 | 22 |
| $H_2$-treated (1.4) | 3.0[b] | 12 | 88 | 20 |
| Standard (3.0) | 6.5 | 16[c] | 89 | 25 |
| $H_2$-treated (3.0) | 4.0 | 12 | 89 | 26 |

[a] The catalyst system consisted of 53 g 4% K on porous $K_2CO_3$ extrudate
[b] The induction period of the catalyst at 1.4 WHSV was difficult to determine since the conversion continued to climb gradually after the initial rapid increase. Thus, the induction period may be longer than stated.
[c] The conversion value levelled off at 12% after 13 hours on-stream.

The examples have been provided merely to illustrate the practice of the invention and should not be read so as to limit the scope of the invention or the appended claims in any way. Reasonable variations and modifications, not departing from the essence and spirit of the invention, are contemplated to be within the scope of the patent protection desired and sought.

That which is claimed is:

1. A dimerization process comprising contacting olefins under dimerization conditions with a composition comprising:
   (a) at least one elemental alkali metal;
   (b) an extruded catalyst support comprising an alkali metal carbonate; wherein component (a) is supported on component (b) to form a catalyst system; and
   (c) wherein said catalyst system is contacted with hydrogen to form a hydrided system.

2. A process according to claim 1 wherein said elemental alkali metal is potassium.

3. A process according to claim 1 wherein said elemental alkali metal is present in an amount within the range of from about 1 to about 20 weight percent based on the total weight of said extruded catalyst support.

4. A process according to claim 1 wherein said alkali metal carbonate is potassium carbonate.

5. A process according to claim 1 wherein said hydrogen contacting is at a temperature within a range of about 50° C. to about 250° C., at a pressure within a range of atmospheric up to about 10,000 psig, for a period of time within the range of about 0.1 second to about 24 hours.

6. A process according to claim 1 further comprising a promoter selected from the group consisting of elemental copper, elemental cobalt, finely divided stainless steel, finely divided glass, and mixtures thereof.

7. A process according to claim 1 wherein said olefin is selected from the group consisting of propylene, 1-butene, 2-butene, isobutylene, 1-pentene, 2-pentene, 1-hexene, 2-hexene, 3-hexene, 1-heptene, 2-heptene, 3-heptene, and mixtures of any two or more thereof.

8. A process according to claim 1 wherein said olefin is propylene.

9. A process according to claim 1 wherein said olefin contacting is carried out at a temperature within the range of about 80° to about 200° C., a pressure within the range of about 100 to about 4,000 psig, and a weight hourly velocity within the range of about 0.1 to about 10.

10. A dimerization process comprising contacting olefins under dimerization conditions with a composition of a hydrided catalyst system produced by a process for the preparation of a hydrided catalyst system comprising:
    (a) preparing a thick paste comprising alkali metal carbonate and liquid;
    (b) forming an extruded catalyst support from said paste;
    (c) drying said extruded catalyst support;
    (d) calcining said dried catalyst support;
    (e) contacting said calcined extruded catalyst support with at least one elemental alkali metal to form a catalyst system; and
    (f) contacting said catalyst system with hydrogen to form a hydrided catalyst system.

11. A process according to claim 10 wherein said alkali metal contacting is under an oxygen-free atmosphere and at a temperature sufficient to cause the elemental alkali metal to melt.

12. A process according to claim 10 wherein said elemental alkali metal is potassium.

13. A process according to claim 10 wherein said elemental alkali metal is present in an amount within the range from about 1 to about 20 weight percent based on the total weight of said extruded catalyst support.

14. A process according to claim 10 wherein said elemental alkali metal carbonate is potassium carbonate.

15. A process according to claim 10 wherein said hydrogen contacting is carried out at a temperature within a range of about 50° C. to about 250° C., at a pressure within a range of atmospheric up to 10,000 psig, for a period of time within the range of from about 0.1 second to about 24 hours.

16. A process according to claim 10 wherein said olefin contacting is carried out at a temperature within the range of about 80° to about 200° C., a pressure within the range of about 100 to about 4,000 psig, and a weight hourly velocity within the range of about 0.1 to about 10.

17. A process for production of 4-methyl-1-pentene comprising contacting propylene under dimerization conditions with a hydrided catalyst system of claim 10.

18. A process according to claim 17 wherein said propylene contacting is carried out at a temperature within the range of about 80° to 200° C., a pressure within the range of about 100 to about 4,000 psig, and weight hourly velocity within the range of about 0.1 to about 10.

* * * * *